United States Patent [19]
Loughhead et al.

[11] Patent Number: 6,110,937
[45] Date of Patent: *Aug. 29, 2000

[54] PHENOXYMETHYL PIPERIDINE DERIVATIVES FOR THE TREATMENT OF NEUROPATHIC PAIN

[75] Inventors: David Garrett Loughhead, Belmont; Xiao-Fa Lin, Mountain View; Robert James Weikert; Lee Allen Flippin, both of Woodside, all of Calif.

[73] Assignee: Syntex USA, Inc., Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/046,951

[22] Filed: Mar. 24, 1998

Related U.S. Application Data

[60] Provisional application No. 60/069,755, Dec. 16, 1997, provisional application No. 60/066,327, Nov. 21, 1997, and provisional application No. 60/042,681, Apr. 3, 1997.

[51] Int. Cl.$^7$ .................... A61K 31/452; C07D 211/18
[52] U.S. Cl. .................... 514/317; 514/331; 546/232; 546/236; 546/240
[58] Field of Search .................... 514/317, 331; 546/232, 236, 240

[56] References Cited

U.S. PATENT DOCUMENTS

| | | |
|---|---|---|
| 3,634,437 | 1/1972 | Todd . |
| 3,709,892 | 1/1973 | Leeming et al. . |
| 4,508,724 | 4/1985 | Taylor, Jr. et al. . |
| 4,822,778 | 4/1989 | Aberg et al. . |
| 4,877,799 | 10/1989 | Drejer et al. . |
| 4,985,446 | 1/1991 | Drejer et al. . |
| 5,019,582 | 5/1991 | Drejer et al. . |
| 5,158,961 | 10/1992 | Jakobsen et al. . |
| 5,210,086 | 5/1993 | George et al. . |
| 5,227,379 | 7/1993 | Jakobsen et al. . |

FOREIGN PATENT DOCUMENTS

| | | |
|---|---|---|
| 1203149 | 8/1970 | United Kingdom . |
| WO 92/02501 | 2/1992 | WIPO . |
| WO 93/15052 | 8/1993 | WIPO . |
| WO 94/13291 | 6/1994 | WIPO . |

OTHER PUBLICATIONS

Arya et al., *Indian J. Chem* (1977), vol. 15B, pp. 1125–1128, "Synthesis & CNS Depressant Activity of Some Pyridyl & Piperidyl Ethers".

Balsamo et al., *J. Med. Chem.* (1987), vol. 30, pp. 222–225, "3–[(2–Ethoxyphenoxy)methyl]piperidine Derivatives. Synthesis and Antidepressant Activity".

Catterall, Trends in Pharmacological Science, vol. 8, No. 2, pp. 57–65 (1987), "Common Modes of Drug Action on Na+ Channels: Local Anesthetics, Antiarrhythmics and Anticonvulsants".

Ragsdale et al, Molecular Pharmacology, vol. 40, No. 5, pp. 756–765 (1991), "Frequency and Voltage–Dependent Inhibition of Type IIA Na+ Channels, Expressed in a Mammalian Cell Line, by Local Anesthetic, Antiarrhythmic, and Anticonvulsant Drugs".

Tolatsky et al, Cardiovascular Drug Review, vol. 7, No. 3, pp. 199–209 (1989), "K+ Channel Blockers and Activators in Cardiac Arrhythmias".

Hondeghem et al, Annual Review. Pharmacol. Toxicol, vol. 24, pp. 387–423 (1984), Antiarrhythmic Agents: The Modulated Receptor Mechanism of Action of Sodium and Calcium Channel–Blocking Drugs.

Roufos et al, Journal of Medical Chemistry, vol. 39, No. 7, pp. 1514–1520 (1996), "A Structure–Activity Relationship Study of Novel Phenylacetamides Which are Sodium Channel Blockers".

Journal of Medical Chemistry, vol. 37, No. 2, pp. 268–274, (1994), "Synthesis and Pharmacological Evaluation of Phenylacetamides as Sodium–Channel Blockers".

*Primary Examiner*—Patricia L. Morris
*Attorney, Agent, or Firm*—Rohan Peries; Janet Kaku

[57] ABSTRACT

Compounds selected from the group of compounds represented by Formula I:

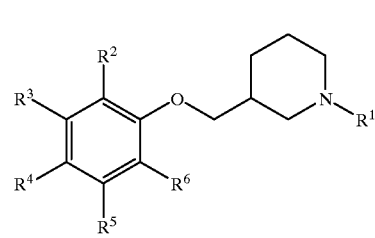

as an individual isomer or as a racemic or non-racemic mixture of isomers, and their pharmaceutically acceptable salts and N-oxides thereof; are sodium channel blockers, and thus exhibit useful pharmacological properties, including utility for the treatment of neuropathic pain conditions.

15 Claims, No Drawings

PHENOXYMETHYL PIPERIDINE DERIVATIVES FOR THE TREATMENT OF NEUROPATHIC PAIN

CROSS-REFERENCE TO RELATED APPLICATION

This application claims benefit under 35 U.S.C. 119(e) of U.S. Provisional application Ser. Nos. 60/069,755, filed Dec. 16, 1997; 60/066,327, filed Nov. 21, 1997; and 60/042,681, filed Apr. 3, 1997.

DESCRIPTION OF THE FIELD

The present invention relates to phenoxymethyl piperidine derivatives, and pharmaceutically acceptable salts and N-oxides thereof, which are sodium channel blockers, and thus exhibit useful pharmacological properties, including utility for the treatment of neuropathic pain conditions. The invention is also directed to formulations and methods for treatment.

BACKGROUND OF THE INVENTION

Neuropathic pain can be described as pain associated with damage or permanent alteration of the peripheral or central nervous system. Clinical manifestations of neuropathic pain include a sensation of burning or electric shock, feelings of bodily distortion, allodynia and hyperalgesia.

Sodium channel-blocking agents have been reported to be effective in the treatment of various disease states, and have found particular use as local anesthetics and in the treatment of cardiac arrhythmias. It has also been reported for many years that sodium channel-blocking agents may also be useful in the treatment of pain, including neuropathic pain; see for example, Tanelian et al. Pain Forum. 1995, 4(2), 75–80. Preclinical evidence demonstrates that sodium channel-blocking agents selectively suppress abnormal ectopic neural firing in injured peripheral and central neurons, and it is via this mechanism that they are believed to be useful for relieving pain. Consistent with this hypothesis, it has been shown that sodium channels accumulate in the peripheral nerve at sites of axonal injury (Devor et al. J. Neurosci. 1993, 132, 1976–1992). Alterations in either the level of expression or distribution of sodium channels within an injured nerve, therefore, have a major influence on the pathophysiology of pain associated with this type of trauma. This concept is supported by the relative success of employing sodium channel modulating agents (e.g., anticonvulsants, local anesthetics) for the treatment of neuropathic pain. However, pain relief has often been obtained concomitantly with numerous adverse events and/or limitations in efficacy which have restricted tolerability of these drugs. It can be seen that a need still exists for an orally active agent that is effective for the treatment of neuropathic pain, but having fewer side effects.

Various phenoxymethyl piperidine derivatives have been described in the patent and non-patent literature. For example, PCT Published Application Nos. WO 92/02501 (Smithkline & French) and WO 93/15052 (Smithkline Beecham) generically discloses various optionally substituted 3-phenoxymethyl piperidine and 3-phenoxyethyl piperidine derivatives, respectively, useful as calcium channel blocking agents.

U.S. Pat. No. 3,634,437 (Todd) discloses optionally substituted 3-phenoxymethyl piperidine compounds, which may be used in the treatment of depressive illness, anxiety, neurotic states and epilepsy. U.S. Pat. No. 3,709,892 (Leeming et al.) discloses substituted 3-phenoxyalkylamines, for example, 3-[(2-cyclohexylethyl)phenoxymethyl]-1-methylpiperidine, which possess gastric antisecretory activity. U.S. Pat. Nos. 4,877,799; 4,985,446; and 5,019,582 (Drejer et al.); and U.S. Pat. Nos. 5,158,961 and 5,227,379 (Jakobsen et al.) disclose 4-phenyl-3-phenoxymethyl piperidine derivatives as calcium overload inhibitors useful in the treatment of anoxia, ischemia, migraine and epilepsy.

U.S. Pat. No. 4,508,724 (Taylor et al.) discloses 3-phenoxymethyl-3-piperidinol derivatives having antiarrhythmic, antidepressant and antihypertensive activity. U.S. Pat. No. 4,822,778 (Aberg et al.) discloses optionally substituted 2-phenoxymethyl piperidine derivatives, particularly N-methyl-2-[(2,6-xyloxy)methyl]-piperidine, having anesthetic and antiarrhythmic activity.

Arya et al. Indian J. Chem. 1977, 15B, 1125–1128 describes the synthesis and pharmacological activity of piperidyl ethers, particularly 3-(4-fluorophenoxymethyl)-1-methylpiperidine, as central nervous system depressants. Balsamo et al. J. Med. Chem. 1987, 30, 222–225, describes the synthesis and antidepressant activity of 3-[(2-ethoxyphenoxy)methyl]-piperidine derivatives.

The disclosures of these and other documents referred to throughout this application are incorporated herein by reference.

SUMMARY OF THE INVENTION

One aspect of the invention relates to compounds represented by Formula I:

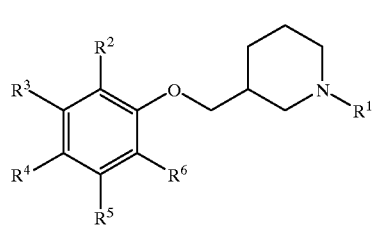

where:
R$^1$ is hydrogen, (C1–4)alkyl, —(CH$_2$)$_m$cycloalkyl, —(CH$_2$)$_m$NR$^7$R$^8$, or —(CH$_2$)$_m$NR$^7$SO$_2$R$^9$;
where:
m is 1 to 3;
R$^2$, R$^3$, R$^5$, and R$^6$ are independently hydrogen, (C1–4) alkyl, or halogen;
R$^4$ is hydrogen, (C1–4)alkyl, hydroxy, alkyloxy, fluoroalkyloxy, halogen, or phenyl or mono- or di-substituted phenyl, the substituents selected from alkyloxy, amino, nitro, or acetylamino;
R$^7$ and R$^8$ are independently hydrogen or (C1–4)alkyl; and
R$^9$ is (C1–4)alkyl;
provided that when R$^1$ is hydrogen at least two of R$^2$, R$^3$, R$^4$, R$^5$, and R$^6$ are other than hydrogen; and further provided that when R$^1$ is methyl and R$^2$, R$^3$, R$^5$ and R$^6$ are hydrogen, R$^4$ is other than fluoro;
or a pharmaceutically acceptable salt or N-oxide thereof, as an individual isomer or as a racemic or non-racemic mixture of isomers.

A second aspect of this invention relates to pharmaceutical compositions containing a therapeutically effective amount of a compound of Formula I or a pharmaceutically acceptable salt or N-oxide thereof, in admixture with one or more pharmaceutically acceptable, non-toxic excipients.

A third aspect of this invention relates to a method for treating a mammal having a disease state which is treatable by administration of a sodium channel-blocker, comprising administering to a mammal in need of a therapeutically effective amount of a compound of Formula I or a pharmaceutically acceptable salt or N-oxide thereof.

DETAILED DESCRIPTION OF THE INVENTION

Definitions

"Alkyl", as in "(C–4)alkyl" means a monovalent branched or unbranched saturated hydrocarbon chain containing 1, 2, 3 or 4 carbons, such that (C1–4)alkyl specifically includes for example, methyl, ethyl, n-propyl, isopropyl, or n-butyl. Similarly, "C1–2", as in "(C1–2)alkyl" means a saturated hydrocarbon chain containing 1 or 2 carbons, such that (C1–2)alkyl specifically includes methyl and ethyl.

"Cycloalkyl" means a monovalent saturated carbocyclic radical containing from three to seven carbon atoms, e.g., cyclopropyl, 2-methylcyclopropyl, cyclobutyl, 3-ethylcyclobutyl, cyclopentyl, cyclohexyl or cyclohexylmethyl.

"Alkyloxy" means —O—R where R is (C1–4)alkyl as defined above.

"Fluoroalkyl" means (C1–4)alkyl as defined above substituted by 1 to 3 fluorine atoms, for example trifluoromethyl, difluoromethyl, 2,2,2-trifluoroethyl, and the like.

"Fluoroalkyloxy" means 'O—R' where R' is fluoroalkyl.

"Halo" means fluoro, chloro, bromo, or iodo, preferably bromo or chloro.

"Optional" or "optionally" means that the subsequently described event or circumstance may or may not occur, and that the description includes instances where the event or circumstance occurs and instances in which it does not.

"Inert organic solvent" or "inert solvent" mean a solvent inert under the conditions of the reaction being described in conjunction therewith including, for example, benzene, toluene, acetonitrile, tetrahydrofuran, dimethylformamide, chloroform ($CHCl_3$), dichloromethane or methylene dichloride ($CH_2Cl_2$), diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Protecting group" means a chemical group that (a) preserves a reactive group from participating in an undesirable chemical reaction; and (b) can be easily removed after protection of the reactive group is no longer required.

"Amino-protecting group" or "N-protecting group" means a protecting group that preserves a reactive amino group that otherwise would be modified by certain chemical reactions. The definition includes the formyl group or lower alkanoyl groups with 2 to 4 carbon atoms, in particular the acetyl or propionyl group, the N-(9-fluorenylmethoxycarbonyl) or "FMOC" group, the allyloxycarbonyl group or other protecting groups derived from halocarbonates such as ($C_6$–$C_{12}$)aryl lower alkyl carbonates (such as the N-benzyloxycarbonyl group derived from benzylchlorocarbonate), or derived from biphenylalkyl halo carbonates, or tertiary alkyl halo carbonates, such as tert-butylhalocarbonates, in particular tert-butylchlorocarbonate, or di(lower)alkyldicarbonates, in particular di(tert-butyl)-dicarbonate.

"Hydroxy-protecting group" means a protecting group that preserves a hydroxy group that otherwise would be modified by certain chemical reactions. Suitable hydroxy-protecting groups include ether-forming groups that can be removed easily after completion of all other reaction steps, such as the benzyl or the trityl group optionally substituted in their phenyl ring, silyl, trialkylsilyl ether groups and the like.

"Leaving group" means a labile group that is replaced in a chemical reaction by another group. Examples of leaving groups are halogen, the optionally substituted phenoxy group, the trifluoromethanesulfonyloxy group, the mesyloxy group, the tosyloxy group or the acyloxy group.

"N-oxide" refers to a stable amine oxide formed at the piperidine nitrogen atom.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture.

The compounds of the invention may possess an asymmetric center at the 3-position of the piperidine, and consequently can exist as a mixture of stereoisomers or as individual (R)— or (S)— stereoisomers. The individual enantiomers may be obtained by resolving a racemic or non-racemic mixture of an intermediate at some appropriate stage of the synthesis, followed by completion of the synthesis in a way that preserves chirality, or by resolution of the compound of Formula I by conventional means. The individual enantiomers, as well as racemic and non-racemic mixtures thereof are encompassed within the scope of the present invention, all of which are intended to be depicted by the structures of this specification unless otherwise specifically indicated. Specific examples of the separation of isomers are set forth in the Examples.

The use of the symbol "(R)" or "(S)" preceding a substituent designates the absolute stereochemistry of that substitutent according to the Cahn-Ingold-Prelog rules (see Cahn et al. *Angew. Chem. Inter.* Edit. 1966, 5, 385, errata 511; Cahn et al. *Angew. Chem.* 1966, 78, 413; Cahn and Ingold *J. Chem. Soc. (London)* 1951, 612; Cahn et al. *Experientia* 1956, 12, 81; Cahn J. *Chem. Educ.* 1964, 41, 116).

"Mammal" includes humans and all domestic and wild mammals, including without limitation, cattle, horses, swine, sheep, goats, dogs, cats, rabbits and the like.

"Pharmaceutically acceptable" means that which is useful in preparing a pharmaceutical composition that is generally safe, non-toxic, and neither biologically nor otherwise undesirable, and includes that which is acceptable for veterinary use as well as human pharmaceutical use.

"Pharmaceutically acceptable salts" refers to those salts which are pharmaceutically acceptable, as defined above, and which possess and retain the desired pharmacological activity of the compounds of Formula I. The compounds of Formula I form acid addition salts by virtue of the presence of the basic piperidine nitrogen atom. Acid addition salts may be formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, p-toluenesulfonic acid, camphorsulfonic acid, 4-methylbicyclo[2.2.2.]oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, tartaric acid and the like. Preferred pharmaceutically acceptable salts are salts formed from inorganic acids. A particularly preferred pharmaceutically acceptable salt is the hydrochloride salt.

"Treatment" means any treatment of a condition in a mammal, particularly a human, and includes:

(I) preventing the disease from occurring in a subject which may be predisposed to the disease, but has not yet been diagnosed as having it;

(ii) inhibiting the condition, i.e., arresting its development; or (iii) relieving the condition, i.e., relieving the symptom of pain.

"Disease state which is treatable by administration of a sodium channel blocker" is intended to cover all disease states which are generally acknowledged in the art to be usefully treated with sodium channel blockers in general, and those disease states which have been found to be usefully treated by the specific sodium channel blocker of our invention, the compounds of Formula I. Such disease states include, but are not limited to, peripheral neuropathies, such as trigeminal neuralgia, postherpetic neuralgia, diabetic neuropathy, glossopharyngeal neuralgia, lumbar and cervical radiculopathies, reflex sympathetic dystrophy and causalgia, and neuropathy secondary to metastatic infiltration, adiposis dolorosa, and burn pain; and central pain conditions following stroke, thalamic lesions and multiple sclerosis.

"Therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

Nomenclature

The naming and numbering of the compounds of this invention is illustrated below. The phenoxymethyl piperidine nucleus of the compound of Formula I is numbered as follows:

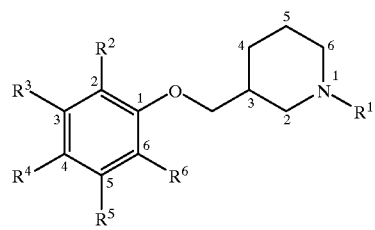

The nomenclature used in this application is generally based on the IUPAC recommendations. However, because a strict adherence to these recommendations would result in the name changing substantially when only a single substituent is changed, the compounds have been named in a form that maintains consistency of nomenclature for the basic structure of the molecule.

For example, a compound of Formula I where $R^1$, $R^2$ and $R^6$ are methyl, $R^3$ and $R^5$ are hydrogen, and $R^4$ is bromo, is named 3-(4-bromo-2,6-dimethylphenoxymethyl)-1-methylpiperidine.

For example, a compound of Formula I where $R^1$, $R^3$ and $R^5$ are hydrogen, $R^2$ and $R^6$ are methyl, and $R^4$ is bromo, is named 3-(4-bromo-2,6-dimethylphenoxymethyl)-piperidine.

Preferred Embodiments

Among the family of compounds of the present invention, certain compounds of Formula I are preferred. Preferred compounds of Formula I are those in which $R^1$ is hydrogen or (C1–4)alkyl, more preferably hydrogen, methyl or ethyl, and most preferably hydrogen or methyl; preferably $R^2$ and $R^6$ are each independently hydrogen or alkyl, more preferably hydrogen or methyl, and most preferably $R^2$ and $R^6$ are each methyl; and preferably $R^3$ and $R^5$ are each independently hydrogen or (C1–4)alkyl, more preferably $R^3$ and $R^5$ are each hydrogen; and $R^4$ is hydrogen or halogen, more preferably hydrogen or bromo, and most preferably bromo.

At present, exemplary particularly preferred compounds include:

3-(4-bromo-2,6-dimethylphenoxymethyl)-1-methylpiperidine;

3-(4-bromo-2,6-dimethylphenoxymethyl)-1-methylpiperidine N-oxide;

(S)-3-(4-bromo-2,6-dimethylphenoxymethyl)-1-methylpiperidine;

3-(4-bromo-2,6-dimethylphenoxymethyl)-piperidine;

(S)-3-(4-bromo-2,6-dimethylphenoxymethyl)-piperidine;

3-(2,6-dimethylphenoxymethyl)-1-methylpiperidine;

3-(2,6-dimethylphenoxymethyl)-1-methylpiperidine N-oxide; and (S)-3-(2,6-dimethylphenoxymethyl)-1-methylpiperidine.

METHODS OF PREPARATION

Compounds of this invention can be made by the methods depicted in the reaction schemes shown below.

The starting materials and reagents used in preparing these compounds are either available from commercial suppliers such as Aldrich Chemical Company, or are prepared by methods known to those skilled in the art following procedures set forth in references such as *Fieser and Fieser's Reagents for Organic Synthesis;* John Wiley and Sons: New York, 1991, Volumes 1–15; Rodd's Chemistry of Carbon Compounds; Elsevier Science Publishers, 1989, Volumes 1–5 and Supplementals; and *Organic Reactions,* John Wiley and Sons: New York, 1991, Volumes 1–40. These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified, if desired, using conventional techniques, including but not limited to filtration, distillation, crystallization, chromatography, and the like. Such materials may be characterized using conventional means, including physical constants and spectral data.

Unless specified to the contrary, the reactions described herein take place at approximately atmospheric pressure over a temperature range from about −78° C. to about 150° C., more preferably from about 0° C. to about 125° C., and most preferably at about room (or ambient) temperature, e.g., about 20° C.

REACTION SCHEME I

Reaction Scheme I describes one method of preparing compounds of Formula I from the reaction of a phenol compound (1) with a piperidine compound (2) where Y is hydrogen or —OY is a leaving group, and $R^1$, $R^2$, $R^3$, $R^4$, $R^5$, and $R^6$ are as defined in the Summary of the Invention:

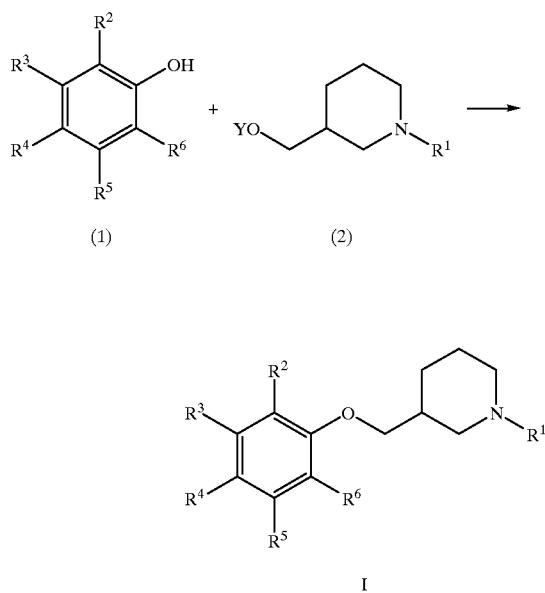

Preparation of Compounds of Formula (1)

In general, the phenol compound (1) is commercially available, for example from Aldrich Chemical Co., or may be prepared by standard methods known to those skilled in the art, for example as is described in detail in Preparation 1.

Preparation of Compounds of Formula (2)

A piperidine compound (2) where Y is hydrogen is commercially available or is prepared by standard methods known to those skilled in the art.

Alternatively, a piperidine compound (2) where —OY is a leaving group, is prepared from the piperidine compound (2) where Y is hydrogen, by converting the hydroxy group to a suitable leaving group. Suitable solvents for the reaction are inert organic solvents, such as halogenated or aromatic hydrocarbons, e.g., dichloromethane, 1,2-dichloroethane, carbon disulfide, and the like, preferably dichloromethane.

Suitable leaving groups are prepared by standard methods, for example by reacting the piperidine compound (2) where Y is hydrogen, with an alkyl or aryl sulfonyl halide, such as benzenesulfonyl chloride, methanesulfonyl chloride, preferably p-toluenesulfonyl chloride. Sulfonyl halides are commercially available or may be prepared by methods such as those described in (i) Langer, R. F. *Can. J. Chem.* 1983, 61, 1583–1592; (ii) Aveta, R. et al. *Gazetta Chimica Italiana* 1986, 116, 649–652; (iii) King, J. F.; Hillhouse, J. H. *Can J. Chem.* 1976, 54, 498; and (iv) Szymonifka, M. J.; Heck, J. V. *Tet. Lett.* 1989, 30, 2869–2872.

An exemplary preparation of a piperidine compound (2) is described in detail in Preparation 2.

Preparation of Compounds of Formula I

A compound of Formula I is prepared by coupling the phenol compound (1) with the piperidine compound (2) where Y is hydrogen. The reaction proceeds in the presence of a combination of an organic phosphine such as triphenylphosphine, and a dialkyl azodicarboxylate such as diethyl azodicarboxylate, under Mitsunobu reaction conditions. Suitable solvents for the reaction are aprotic organic solvents such as dimethylformamide, N-methyl pyrrolidone, or tetrahydrofuran, preferably tetrahydrofuran.

Alternatively, a compound of Formula I is prepared by coupling the phenol compound (1) with a piperidine compound (2) where —OY is a leaving group. The reaction is carried out under an inert atmosphere in the presence of base, e.g., cesium carbonate, sodium carbonate or potassium carbonate, preferably cesium carbonate. Suitable solvents for the reaction are aprotic organic solvents, such as dimethylformamide, N-methyl pyrrolidone, tetrahydrofuran, and the like, preferably dimethylformamide.

An exemplary preparation of a compound of Formula I is described in detail in Example 2.

REACTION SCHEME II

Reaction Scheme II describes an alternative method of preparing a compound of Formula I through an N-protected piperidine intermediate of formula (3) where P is an amino protecting group, and $R^1$, $R^2$, $R^3$, $R^4$, $R^5$, and $R^6$ are as defined in the Summary of the Invention:

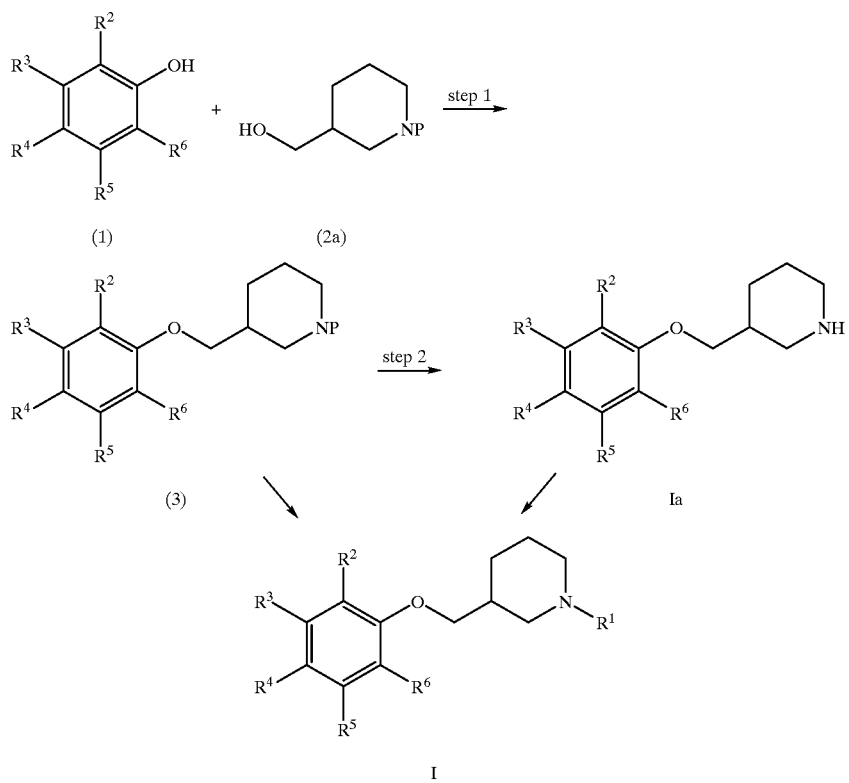

Preparation of Compounds of Formula (1)

A phenol compound (1) is prepared as described in Reaction Scheme I.

Preparation of Compounds of Formula (2a)

An N-protected piperidine compound (2a) where P is an amino-protecting group, is prepared by conventional means, for example by treating the piperidine compound (2) where $R^1$ and Y are each hydrogen, with a suitable amino-protecting agent, such as acyl halide, sulfonyl halide, dialkyl dicarbonate (e.g., di-tert-butyl dicarbonate) or alkylhalocarbonate, preferably di-tert-butyl dicarbonate. Suitable solvents for the reaction are aprotic organic solvents such as dimethylformamide, N-methyl pyrrolidone or tetrahydrofuran, preferably tetrahydrofuran.

An exemplary preparation of an N-protected piperidine compound of formula (2a) is described in detail in Preparation 2B.

Preparation of Compounds of Formula (3)

An N-protected phenoxymethyl piperidine compound (3) is prepared by coupling the phenol compound (1) with the N-protected piperidine compound (2a), and utilizing the reaction conditions described for the preparation of compounds of Formula I in Reaction Scheme I.

An exemplary preparation of an N-protected phenoxymethyl piperidine compound of formula (3) is described in detail in Preparation 3.

Preparation of Compounds of Formula Ia where $R^1$ is Hydrogen

A compound of Formula Ia where $R^1$ is hydrogen is prepared by removing the N-protecting group of the compound of formula (3). The deprotecting reaction proceeds in the presence of a strong organic acid, preferably trifluoroacetic acid, in an inert organic solvent such as halogenated or aromatic hydrocarbons, e.g., benzene, dichloromethane, 1,2-dichloroethane, carbon disulfide, and the like, preferably dichloromethane. The reaction can also proceed in the presence of a strong base, for example sodium hydroxide or potassium hydroxide, in a mixture of water and a protic organic solvent, e.g., methanol or ethanol, preferably methanol.

An exemplary preparation of a compound of Formula Ia where $R^1$ is hydrogen, is described in detail in Example 1.

Preparation of Compounds of Formula I where $R^1$ is Methyl

A compound of Formula I where is $R^1$ is methyl may be prepared by the method described in Reaction Scheme I.

Alternatively, a compound of Formula I where is $R^1$ is methyl is prepared by reducing the N-protecting group of the compound of formula (3) where P is an amino-protecting group such as a carbamate (e.g., tert-butoxycarbonyl), with borane, borane complexes or a metal hydride such as lithium aluminum hydride. The reaction proceeds under an inert atmosphere in an aprotic organic solvent such as diethyl ether, dioxane or tetrahydrofuran, preferably tetrahydrofuran.

Alternatively, the compound of Formula I where is $R^1$ is methyl is prepared by reductive alkylation of the compound of Formula Ia, for example with formaldehyde and formic acid under Eschweiler-Clarke reaction conditions.

Exemplary preparations of a compound of Formula I where is $R^1$ is methyl are described in detail in Examples 2 and 3.

Preparation of Compounds of Formula I where $R^1$ is (C2–4)alkyl or $(CH_2)_m$cycloalkyl A compound of Formula I where $R^1$ is (C2–4)alkyl or $(CH_2)_m$cycloalkyl is prepared by acylation of the compound of Formula Ia by reaction with an acyl halide (e.g., cyclopropanecarbonyl chloride or acetyl chloride, preferably cyclopropanecarbonyl chloride), in the presence of an aqueous base, e.g., sodium bicarbonate or potassium bicarbonate. The reaction proceeds at ice cold temperatures under an inert atmosphere in an aprotic organic solvent such as dimethylformamide, ethyl acetate, N-methyl pyrrolidone or tetrahydrofuran, preferably ethyl acetate. The residue is subsequently treated with a suitable reducing agent such as metal hydride, e.g., lithium aluminum hydride, in an aprotic organic solvent such as tetrahydrofuran.

An exemplary preparation of a compound of Formula I where is $R^1$ is $(CH_2)_m$cycloalkyl is described in detail in Example 4.

Preparation of Compounds of Formula I where $R^1$ is $-(CH_2)_m NR^7R^8$

A compound of Formula I where $R^1$ is $-(CH_2)_m NR^7R^8$ is prepared by reacting the compound of Formula Ia with a compound of the formula $Cl(CH_2)_{m-1}COCl$ in a two-phase system utilizing an alkaline aqueous solvent such as aqueous sodium bicarbonate or potassium bicarbonate for the first phase; and an inert organic solvent, for example diethyl ether, hexane, and the like, preferably diethyl ether for the second phase. The reaction is carried out at about room temperature for about 30 minutes to 3 hours, preferably 2 hours. The product is dissolved in a protic organic solvent such as methanol or ethanol, cooled in an ice bath, treated with a compound of formula $HNR^7R^8$, and subsequently treated with a suitable reducing agent such as metal hydride, e.g., lithium aluminum hydride, under an inert atmosphere in an aprotic organic solvent such as tetrahydrofuran.

An exemplary preparation of a compound of Formula I where is $R^1$ is $-(CH_2)_m NR^7R^8$ is described in detail in Example 5.

Preparation of Compounds of Formula I where $R^1$ is $-(CH_2)_m NHSO_2R^9$

A compound of Formula I where $R^1$ is $-(CH_2)_m NHSO_2R^9$ is prepared by reacting a compound of Formula Ia with a sulfonamide compound of formula $Cl(CH_2)_m NHSO_2R^9$ in the presence of an inorganic base such as potassium carbonate or sodium carbonate, preferably potassium carbonate. Suitable solvents for the reaction are aprotic solvents, such as dimethylformamide, N-methyl pyrrolidone, or tetrahydrofuran, preferably tetrahydrofuran.

An exemplary preparation of a compound of Formula I where is $R^1$ is $-(CH_2)_m NHSO_2R^9$, is described in detail in Example 6.

REACTION SCHEME III

Reaction Scheme III describes alternative methods of preparing compounds of Formula I from the corresponding intermediate phenol compounds of formula (1b) where $R^4$ is hydroxy; or formula (1d) where $R^4$ is alkyloxy or fluoroalkyloxy; or formula (1f) where $R^4$ is phenyl or mono- or di-substituted phenyl; and $R^1$ is other than hydrogen, $R^2$, $R^3$, $R^5$ and $R^6$ are as defined in the Summary of the Invention:

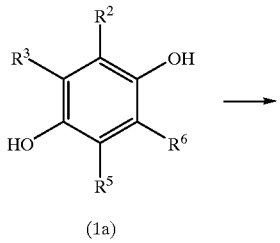

(1a)

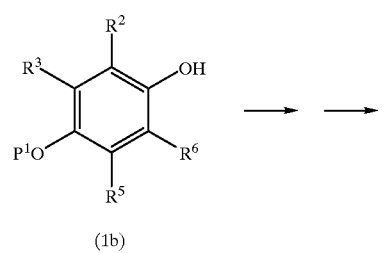

(1b)

where $P^1$ is a hydroxy protecting group

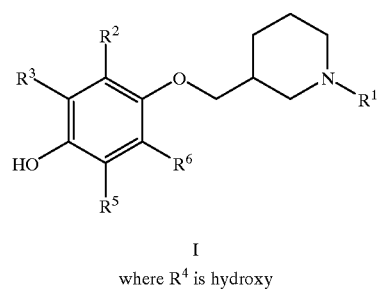

I where $R^4$ is hydroxy

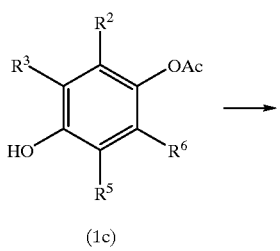

(1c)

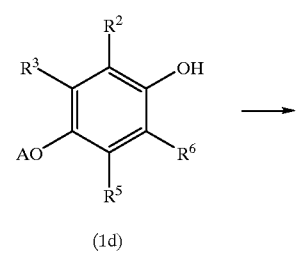

(1d)

where A is alky or fluoroalkyl

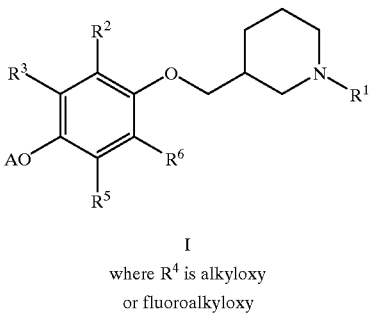

I
where $R^4$ is alkyloxy
or fluoroalkyloxy

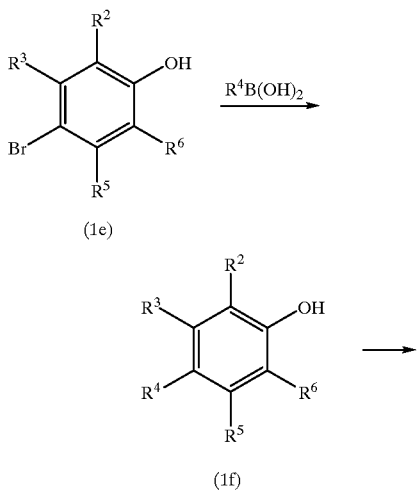

(1e)

(1f)
where $R^4$ is phenyl or substituted phenyl

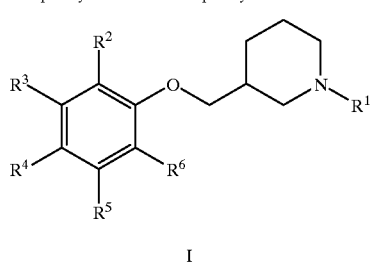

I

Preparation of Compounds of Formula I where $R^4$ is Hydroxy

A compound of Formula I where $R^4$ is a hydroxy is prepared through an intermediate phenol compound (1b) where $P^1$ is a hydroxy-protecting group.

The intermediate phenol compound (1b) is prepared by protecting the hydroxy group of a compound of formula (1a) by standard methods known in the art, for example Corey, E. J.; Venkateswarlu, A. *J. Am. Chem. Soc.*, 1972, 94, 6190. Suitable hydroxy protecting groups include alkylsilyl groups, e.g., tert-butyldimethylsilyl.

Proceeding as in Reaction Scheme I or II, but substituting the hydroxy-protected phenol compound (1b) for the phenol compound (1) and coupling with the piperidine compound (2) or (2a) results in a hydroxy-protected phenoxymethyl piperidine compound. The compound of Formula I where $R^4$ is a hydroxy, is subsequently prepared by cleaving the protecting group by methods conventional and selective for the removal of the hydroxy-protecting groups such as alkylammonium halides, e.g., tert-butylammonium fluoride in the presence of an organic acid, e.g., acetic acid, in an aprotic solvent such as tetrahydrofuran.

An exemplary preparation describing in detail the removal of the hydroxy-protecting group to form a compound of Formula I where is $R^4$ is hydroxy is in Example 7.

Preparation of Compounds of Formula I where $R^4$ is Alkyloxy or Fluoroalkyloxy A compound of Formula I where $R^4$ is alkyloxy or fluoroalkyloxy is prepared through an intermediate phenol compound (1d) where A is alkyl or fluoroalkyl.

An intermediate phenol compound (1d) is prepared by reacting the p-hydroxy phenyl acetate compound (1c) with an alkylating agent of formula AY, where A is alkyl or fluoroalkyl and Y is a leaving group such as halo, alkylhalosulfonate or aryl sulfonate, e.g., trifluoroethyltriflate. The reaction proceeds under basic conditions such as potassium carbonate or sodium carbonate, in an aprotic organic solvent such as butanone, tetrahydrofuran or dimethylformamide, preferably butanone. The acetate group is subsequently hydrolyzed under alkaline conditions, utilizing an alkoxide anion such as sodium methoxide, e.g., in a protic organic solvent such as methanol or ethanol, preferably methanol. An exemplary preparation of the intermediate phenol compound (1d) is described in detail in Preparation 1B.

Proceeding as in Reaction Scheme I or II, but substituting the intermediate phenol compound (1d) for the phenol compound (1) and coupling with the piperidine compound (2) or (2a), the compound of Formula I where $R^4$ is alkyloxy or fluoroalkyloxy is prepared.

Preparation of Compounds of Formula I where $R^4$ is Phenyl or Substituted Phenyl A compound of Formula I where $R^4$ is phenyl or mono- or di-substituted phenyl is prepared through an intermediate phenol compound (1f) where $R^4$ is phenyl or mono- or di-substituted phenyl.

The intermediate phenol compound (1f) is prepared by the palladium-catalyzed coupling of the bromo compound of formula (1e) with an arylboronic acid such as nitrophenylboronic acid and a zero valent palladium catalyst such as tetrakis-(triphenylphosphine)palladium(0) in the presence of an inorganic base such as sodium carbonate or potassium carbonate. Suitable solvents for the reaction are aprotic solvents, such as dimethylformamide, N-methyl pyrrolidone, or tetrahydrofuran, preferably tetrahydrofuran.

Proceeding as in Reaction Scheme I or II, but substituting the intermediate phenol compound (1f) for the phenol compound (1) and coupling with the piperidine compound (2) or (2a), the compound of Formula I where $R^4$ is phenyl or mono- or di-substituted phenyl is prepared.

Conversion of Compounds of Formula I to Other Compounds of Formula I

The compounds of Formula I where $R^4$ is phenyl or mono- or di-substituted phenyl; and $R^1$ is other than hydrogen, $R^2$, $R^3$, $R^5$ and $R^6$ are as defined in the Summary of the Invention may be prepared from other compounds of Formula I:

A. For example, a compound of Formula I where $R^4$ is 3-methoxyphenyl is prepared by the palladium-catalyzed coupling of a compound of Formula I where $R^4$ is bromo with an arylboronic acid such as nitrophenylboronic acid and a zero valent palladium catalyst such as tetrakis (triphenylphosphine)palladium(0) in the presence of an inorganic base such as sodium carbonate or potassium carbonate. Suitable solvents for the reaction are aprotic solvents, such as dimethylformamide, N-methyl pyrrolidone, or tetrahydrofuran, preferably tetrahydrofuran.

An exemplary preparation of a compound of Formula I where $R^4$ is 3-methoxyphenyl is described in detail in Example 8.

B. For example, a compound of Formula I where $R^4$ is 3-aminophenyl is prepared by reducing the nitro group of the 3-nitrophenyl compound (prepared as described above in Reaction Scheme III where $R^4$ is phenyl or substituted phenyl) to an amino group. Suitable nitro group reducing conditions include iron metal with ammonium chloride in ethanol/water, nickel boride in acidic methanol or catalytic hydrogenation using a platinum or palladium catalyst (e.g., platinum oxide or palladium on carbon) in an alcoholic solvent such as methanol or ethanol, preferably ethanol). The reaction proceeds under an inert atmosphere.

An exemplary preparation of a compound of Formula I where $R^4$ is 3-aminophenyl is described in detail in Example 9.

C. For example, a compound of Formula I where $R^4$ is 3-acetylaminophenyl is prepared by treating the 3-aminophenyl compound described above in Section B with an acylating agent such as an acid halide or acid anhydride (e.g., acetic anhydride) in the presence of an organic base (e.g., triethylamine or pyridine, preferably pyridine). Suitable solvents for the reaction are inert organic solvents, such as halogenated or aromatic hydrocarbons, e.g., benzene, dichloromethane, 1,2-dichloroethane, carbon disulfide, and the like, preferably dichloromethane.

An exemplary preparation of a compound of Formula I where $R^4$ is 3-acetylaminophenyl is described in detail in Example 10.

REACTION SCHEME IV

Reaction Scheme IV describes the preparation of an N-oxide of a compound of Formula I where $R^1$ is other than hydrogen, and $R^2$, $R^3$, $R^4$, $R^5$ and $R^6$ are as defined in the Summary of the Invention:

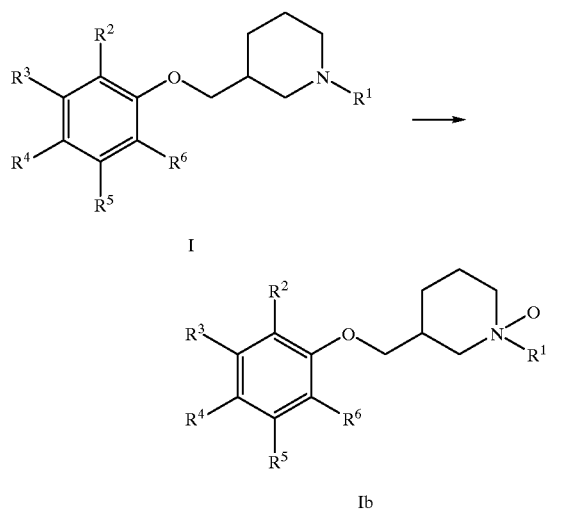

An N-oxide compound of Formula Ib is prepared by the oxidation of a compound of Formula I with a suitable oxidizing agent such as peroxide or peracid, e.g., m-chloroperbenzoic acid or hydrogen peroxide, preferably m-chloroperbenzoic acid. Suitable solvents for the reaction are inert organic solvents, such as halogenated or aromatic hydrocarbons, e.g., benzene, dichloromethane, 1,2-dichloroethane, and the like, preferably dichloromethane.

An exemplary preparation of the N-oxide compound of Formula Ib is described in detail in Example 11.

Resolution of Compounds of Formula I

A compound of Formula I may be resolved into its individual (S)— and (R)— enantiomers by conventional resolution means; for example separation (e.g., fractional crystallization) of the diastereomeric salts formed by combining the compound of Formula I with an optically active acid, at temperatures between 0° C. and the reflux temperature of the solvent employed for fractional crystallization. Exemplary of such optically active acids are camphor-10-sulfonic acid, 2-bromo-camphor-10-sulfonic acid, camphoric acid, menthoxyacetic acid, tartaric acid, dibenzoyltartaric acid, malic acid, diacetyltartaric acid, pyrrolidine-5-carboxylic acid, and the like. The separated pure diastereomeric salts may then be cleaved by standard means, such as treatment with a base, to afford the (S)— or (R)— enantiomer of a compound of Formula I.

Alternatively, the (S)— or (R)— enantiomer of a compound of Formula I may be prepared by conventional means such as synthesis with a single stereoisomer intermediate and reacting in such a manner that the chiral center is unaffected. For example, compounds of Formula I may be prepared starting with an optically pure hydroxymethyl piperidine compounds following the procedures of described in Reaction Scheme II. An optically pure hydroxymethyl piperidine compound can be obtained via reduction of an enantiomer of an ethyl piperidinecarboxylate derivative. The resolution of ethyl 3-piperidinecarboxylate with an optically active acid salt to form the optically active (R)— and (S)— enantiomers is well exemplified in the chemical literature, for example, Zeng et al. *Chirality* 1995, 7, 90–95; and Akkerman et al. *Rec. Trav. Chim.* Pays-Bas 1951, 70, 899–916.

Preferred Processes

In summary, compounds of Formula I are prepared according to the following last steps:

1. A process for preparing compounds of Formula I comprises: reacting a compound of the formula:

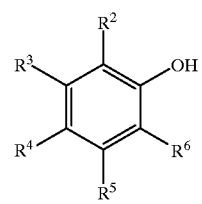

where $R^2$, $R^3$, $R^4$, $R^5$, and $R^6$ are as defined in the Summary of the Invention; with a compound of the formula:

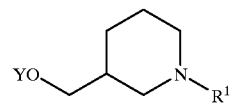

where Y is hydrogen or —OY is a leaving group, and $R^1$ is as defined in the Summary of the Invention.

2. Alternatively, a process for preparing compounds of Formula I comprises: reacting a compound of the formula

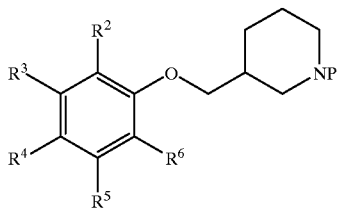

where P is an amino-protecting group, and $R^2$, $R^3$, $R^4$, $R^5$, and $R^6$ are as defined in the Summary of the Invention; with a reducing agent.

3. Alternatively, a process for preparing compounds of Formula I comprises: reacting a compound of the formula:

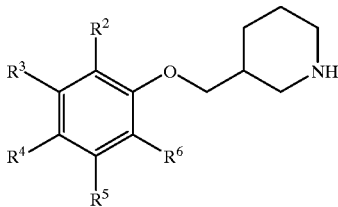

where $R^2$, $R^3$, $R^4$, $R^5$, and $R^6$ are as defined in the Summary of the Invention; with (A) formaldehyde and formic acid, to give a compound of Formula I where $R^1$ is methyl; or (B) an acyl chloride, followed by reduction to give a compound of Formula I where $R^1$ is alkyl or cycloalkyl; or (C) a compound of the formula $Cl(CH_2)_{m-1}COCl$ and $HNR^7R^8$, followed by reduction to give a compound of Formula I where $R^1$ is $—(CH_2)_m NR^7R^8$; or (D) a compound of the formula $Cl(CH_2)_m NSO_2R^9$, to give a compound of Formula I where $R^1$ is $—(CH_2)_m NSO_2R^9$.

4. Alternatively, a process for preparing compounds of Formula I where $R^1$ is other than hydrogen, comprises: reacting a compound of Formula I with an oxidizing agent to give an N-oxide of a compound of Formula I; or reacting a compound of Formula I with a strong acid to give a pharmaceutically acceptable salt of a compound of Formula I.

General Utility and Administration

General Utility

The compounds of Formula I and their pharmaceutically acceptable salts and N-oxides have been found to possess valuable pharmacological properties. In particular, they have been shown to be useful as sodium channel blockers in standard laboratory tests. The ability of compounds of Formula I to block sodium channels may be demonstrated by a variety of assays known to those of ordinary skill in the art, for example the in vitro assay of Kourtney and Strichartz, *Local Anesthetics;* Springer-Verlag, New York, 1987 or modifications thereof, described in Example 18; the mechanical allodynia in vivo assay described in Example 19; the cold allodynia in vivo assay described in Example 20; the mechanical hyperalgesia in vivo assay described in Example 21; and the thermal hyperalgesia in vivo assay described in Example 22. Accordingly, these compounds and pharmaceutically acceptable compositions containing them are useful in the regulation of physiological phenomena related to sodium channel blockade and are potentially effective therapies for a variety of chronic neuropathic pain syndromes, including but not limited to, peripheral neuropathies such as trigeminal neuralgia, postherpetic neuralgia, diabetic neuropathy, glossopharyngeal neuralgia, lumbar and cervical radiculopathies, reflex sympathetic dystrophy and causalgia, and neuropathy secondary to metastatic infiltration, adiposis dolorosa, and burn pain; and central pain conditions following stroke, thalamic lesions and multiple sclerosis.

Clinical evidence supports a therapeutic role for sodium channel blockers in the treatment of neuropathic pain originating in the peripheral nervous system, including cervical and lumbar radiculopathies (Nagaro et al. *Japanese J. Anesthesiology* 1995, 44, 862–867; Ferrante et al. *Anesthesia & Analgesia* 1996, 82, 91–97), diabetic neuropathy (Dejgard et al. *Lancet* 1988, 1, 9–11), neuralgic pain (Marchettini et al. *Pain* 1992, 48, 377–382; Rowbotham, M. C. et al. *Neurology* 1991, 41, 1024–1028), and peripheral nerve injury (Chabal et al. *Anesthesiology* 1992, 76, 513–517). In addition to these conditions, two retrospective clinical studies have found that these agents provided partial to complete relief of pain associated with reflex sympathetic dystrophy and causalgia (Edwards et al. *Regional Anesthesia* 1985, 10, 1–6; Galer et al. *Neurology* 1993, 43, 1233–1235). Central pain conditions following stroke, thalamic lesions and multiple sclerosis have also responded to treatment by these agents (Edmondson et al. *Southern Med. J.* 1993, 86, 1093–1096; Nagaro et al. 1995 idem).

Clinical and experimental evidence support a therapeutic role for sodium channel blockers in the treatment of cancer pain (Nagaro et al. 1995 idem; Chong et al. J. *Pain & Symptom Management* 1997, 13, 112–117) and in many chronic, non-malignant pain states, including pain of musculoskeletal origin, adiposis dolorosa (Atkinson et al. *International J. Obesity* 1982, 6, 351–357; Petersen, P. and Kastrup, J. *Pain* 1987, 28, 77–80) and cluster headaches (Robbins et al. *Headache* 1995, 35, 83–84) or migraine headaches (Kudrow et al. *Headache* 1995, 35, 79–82; Maizels et al. *JAMA* 1996, 276, 319–321).

Experimental evidence supports a therapeutic role for sodium channel blockers as neuroprotective or cerebroprotective agents and may provide an effective strategy against neurological damage (e.g., ischemia, head trauma, hypoxia, stroke). Long-term beneficial effects on neurological deficit, cognitive deficit and brain damage after middle cerebral artery occlusion (Smith, S. E. *Neuroscience* 1997, 77,1123–1135); neuroprotective, anticonvulsant and sedative properties in transient global cerebral ischemia (Doble, A. *Neurology* 1996, 47 (6 Suppl 4), S233–41); and reduction of ischemic brain damage after acute subdural hematoma model (Tsuchida E. et al., *J. of Neurosurgery* 1996, 85, 104–111) were demonstrated in rodent models.

Clinical evidence supports a therapeutic role for sodium channel blockers for pre-emptive analgesia at low, non-toxic, systemic concentrations (Strichartz, G. *Anesthesiology* 1995, 83, 654–655). In many surgical intervention procedures, hypersensitivity reactions to tactile and painful stimuli can result from disruption to soft tissue or a major nerve. This can be apparent for several weeks or even longer following initial surgery. Since sodium channels play a fundamental role in neuronal hyperexcitability, pre-emptive treatment with a channel blocker may limit any potential hypersensitivity reaction to the surgery.

General Administration

In applying the compounds of this invention to treatment of the above conditions, administration of the active compounds and salts described herein can be via any of the accepted modes of administration, including oral (including sublingual or buccal), nasal, parenteral and otherwise systemic routes of administration. Any pharmaceutically acceptable mode of administration can be used, including solid, semi-solid or liquid dosage forms, such as, for example, tablets, suppositories, pills, capsules, powders, liquids, suspensions, sprays or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will, of course, be dependent on the subject being treated, the severity of the affliction, the manner of administration and the judgment of the prescribing physician. However, an effective dose for oral, parenteral and otherwise systemic routes of administration is in the range of about 0.1–5 mg/kg/day. For an average 70 kg human, this would amount to about 10–350 mg per day.

One of ordinary skill in the art of treating such diseases will be able, without undue experimentation and in reliance upon personal knowledge and the disclosure of this application, to ascertain a therapeutically effective amount of a compound of Formula I for a given disease.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like. The active compound as defined above may be formulated as suppositories using, for example, polyalkylene glycols, acetylated triglycerides and the like as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. The composition or formulation to be administered will, in any event, contain a quantity of the active compound(s) in an amount effective to alleviate the symptoms of the subject being treated.

Dosage forms or compositions containing active ingredient (compounds of Formula I or its salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%–95% active ingredient, more preferably 2–80%, most preferably 5–50%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences;* Mack Publishing Company, Easton, Pa., 19th Edition, 1995.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Examples 12–17.

EXAMPLES

The following preparations and examples are given to enable those skilled in the art to more clearly understand and practice the present invention. They should not be considered as limiting the scope of the invention, but merely as being illustrative and representative thereof.

Preparation 1

Preparation of Compounds of Formula (1)

A. Preparation of (1) where $R^2$ and $R^6$ are Methyl, $R^3$ and $R^5$ are Hydrogen, and $R^4$ is 3-nitrophenyl To a solution of 4-bromo-2,6-dimethylphenol (2.58 g, 12.8 mmol) and 3-nitrophenylboronic acid (2.08 g, 12.5 mmol) in toluene (50 mL) were added tetrakis (triphenylphosphine)palladium(0) (0.48 g, 0.42 mmol) and 2M sodium carbonate (6.3 mL, 13 mmol). The mixture was stirred at 100° C. for 22 hours at which time additional palladium catalyst (150 mg) was added. The mixture was heated for another 20 hours and then cooled to room temperature. The mixture was partitioned between water and ethyl acetate. The organic layer was dried and concentrated. The residue was purified on silica gel, eluting with 12% ethyl acetate in hexanes, to provide 4-(3-nitrophenyl)-2,6-dimethylphenol as a yellow solid (0.932 g, 31%).

B. Preparation of (1d) where $R^2$ and $R^6$ are Methyl, $R^3$ and $R^5$ are Hydrogen, and A is 2,2,2-Trifluoroethyl 2,2,2-Trifluoroethyl triflate (1.02 g, 4.40 mmol) and potassium carbonate (1.10 g, 1.01 mmol) were added to a solution of 4-hydroxy-2,6-dimethylphenyl acetate (673 mg, 3.73 mmol) in 2-butanone (15 mL). The mixture was stirred at 70° C. for 72 hours, then cooled to room temperature and concentrated. The residue was partitioned between water and ethyl acetate. The organic layer was washed twice with water and brine and dried. The solvent was removed in vacuo and the residue purified on silica gel, eluting with 10% ethyl acetate in hexanes, to give 2,6-dimethyl-4-(2,2,2-trifluoroethoxy)phenyl acetate (733 mg, 75%).

The 2,6-dimethyl-4-(2,2,2-trifluoroethoxy)phenyl acetate (733 mg, 2.80 mmol) in methanol (10 mL) was treated with sodium metal and stirred at room temperature overnight. The solvent was removed and the residue partitioned between ethyl acetate and water. The organic layer was washed twice with brine and dried. The solvent was removed to give 2,6-dimethyl-4-(2,2,2-trifluoroethoxy)phenol.

Preparation 2

Preparation of Compounds of Formula (2)

A. Preparation of (2) where $R^1$ is Methyl and Y is P-Toluenesulfonyl

A solution of (R)-3-hydroxymethyl-1-methylpiperidine (2.6 g, 20 mmol) in dichloromethane (70 mL) was cooled to 5° C. and tosyl chloride (3.8 g, 20 mmol) was added in portions during 15 minutes. After the addition was complete, the reaction was allowed to warm to room temperature and was stirred for 20 hours. The reaction mixture was then concentrated and the residue partitioned between 10% potassium hydroxide (50 mL) and ether (100 mL). The ether layer was removed and the aqueous phase extracted once again with ether (50 mL). The combined ether layers were dried over magnesium sulfate and concentrated to afford (R)-3-tosyloxymethyl-1-methylpiperidine as a white solid (2.4 g, 42%), m.p. 74.5–81.0° C.

B. Preparation of (2a) where P is tert-Butoxycarbonyl

Ethyl 3-piperidinecarboxylate (200 g) was combined with (−)-D-tartaric acid (191 g) in hot 95% ethanol. The resulting precipitate was filtered and recrystallized six times from 95% ethanol to give (S)-ethyl 3-piperidinecarboxylate D-tartrate salt of high optical purity as determined by chiral HPLC analysis.

Aqueous sodium hydroxide (31.2 g in 100 mL water) was added to a solution of (S)-ethyl 3-piperidinecarboxylate D-tartrate salt (100 g) in tetrahydrofuran (1 L) while maintaining a temperature below 8° C. After the addition was complete, di-tert-butyl dicarbonate (100 g) in tetrahydrofuran (200 mL) was added dropwise at a temperature maintained below 10° C. After 2.5 hours, the reaction was partitioned between ethyl acetate (2 L) and water (2 L). The organic layer was removed, washed with water (2×500 mL) and brine (300 mL), dried over magnesium sulfate, and concentrated. The residue was dissolved in dry tetrahydrofuran (1 L) and cooled to 10° C.

Lithium borohydride (200 mL of a 2.0M solution in tetrahydrofuran) was added dropwise at a temperature maintained below 10° C., and the reaction stirred at room temperature for 24 hours. Additional lithium borohydride solution (20 mL) was added and the reaction mixture stirred at room temperature for another 20 hours. Sodium sulfate decahydrate (50 g) was slowly added, and the mixture was filtered. The solids were washed with ethyl acetate (200 mL), concentrated, and partitioned between ether (1 L) and brine (500 mL). The ether layer was dried over magnesium sulfate and concentrated to give (S)-N-(tert-butoxycarbonyl)-3-hydroxymethylpiperidine as a white solid (47 g).

Preparation 3

Preparation of Compounds of Formula (3)

A. Preparation of (3) where $R^2$ and $R^6$ are Methyl, $R^3$, $R^4$, and R5 are Hydrogen, and P is tert-Butoxycarbonyl (S)-N-(tert-Butoxycarbonyl)-3-hydroxymethylpiperidine (11.0 g, 51.1 mmol) and triphenylphosphine (14.7 g, 56.2 mmol) were added under a dry nitrogen atmosphere to a solution of 2,6-dimethylphenol (6.24 g, 51.1 mmol) dissolved in dry tetrahydrofuran (200 mL). The solution was cooled in an ice bath and diethyl azodicarboxylate (6.9 mL, 56.2 mmol) in tetrahydrofuran (40 mL) was added dropwise at a rate which kept the temperature below 10° C. After the addition was complete, the mixture was allowed to stir at room temperature for 48 hours. The reaction mixture was partitioned between ethyl acetate (1 L) and water (1 L). The organic layer was washed with water (3×300 mL), brine (200 mL), dried, filtered and chromatographed on silica gel, eluting with ethyl acetate/hexanes (9:1) and concentrated to give (S)-(N-tert-butoxycarbonyl)-3-(2,6-dimethylphenoxymethyl)piperidine as a clear oil (13.0 g, 45.2%).

B. Preparation of (3) where $R^2$ and $R^6$ are Methyl, $R^3$ and $R^5$ are Hydrogen, $R^4$ is Bromo, and P is tert-Butoxycarbonyl A solution of diethyl azodicarboxylate (16.1 mL, 102.2 mmol) in tetrahydrofuran (50 mL) was added dropwise during 1.5 hours to an ice cold solution of (S)-N-(tert-butoxycarbonyl)-3-hydroxymethylpiperidine (20.0 g, 92.9 mmol), 4-bromo-2,6 dimethylphenol (18.7 g, 92.9 mmol), and triphenylphosphine (26.8 g, 102.2 mmol) in tetrahydrofuran (300 mL), while maintaining the temperature below 10° C. After the addition was complete, the reaction was stirred at room temperature for 48 hours and partitioned between ethyl acetate (1 L) and water (1 L). After extracting the aqueous phase with additional ethyl acetate (2×200 mL), the combined ethyl acetate layers were washed with brine (250 mL), dried over magnesium sulfate, and concentrated to afford a thick yellow oil. The oil was combined with hexane (500 mL) and ether (50 mL) and stirred for 30 minutes. The resulting white precipitate was removed by filtration and washed with additional hexane (50 mL). The combined filtrates were concentrated to give crude (S)-N-(tert-butoxycarbonyl)-3-(4-bromo-2,6-dimethylphenoxymethyl)piperidine as a clear yellow oil (44 g).

Example 1

Preparation of Compounds of Formula Ia
A. Preparation of Ia where $R^2$ and $R^6$ are Methyl, $R^3$ and $R^5$ are Hydrogen, and $R^4$ is Bromo Trifluoroacetic acid (80 mL) was added dropwise during 20 minutes to a solution of (S)-N-(tert-butoxycarbonyl)-3-(4-bromo-2,6-dimethylphenoxymethyl)piperidine (37.0 g, 92.9 mmol) in dichloromethane (250 mL) at a temperature of 5° C. After the addition was complete, the reaction mixture was stirred at room temperature for 2 hours. The solvent was then evaporated and the residue partitioned between 25% aqueous sodium hydroxide (200 mL) and ether (500 mL). The organic layer was removed and the aqueous phase extracted with additional ether (2×300 mL). The combined ether layers were washed with brine (100 mL), stirred over magnesium sulfate for 2 hours, and filtered to give a solution of (S)-3-(4-bromo-2,6-dimethylphenoxymethyl)piperidine.

The (S)-3-(4-bromo-2,6-dimethylphenoxymethyl) piperidine in ether was treated with 1M solution of hydrochloric acid in ether (102 mL). The resulting white precipitate was filtered, and dried in vacuo to yield (S)-3-(4-bromo-2,6-dimethylphenoxymethyl)-piperidine hydrochloride (29.5 g, 94.5%), m.p.>280° C.

B. Similarly, replacing (S)-N-(tert-butoxycarbonyl)-3-(4-bromo-2,6-dimethylphenoxymethyl)piperidine with other compounds of formula (3), and following the procedures of Example 1A above, the following compounds of Formula Ia were prepared:

3-(4-bromo-2,6-dimethylphenoxymethyl)piperidine hydrochloride, m.p. 263.3–264.7° C.;

3-(2,6-dimethylphenoxymethyl)piperidine hydrochloride, m.p. 204.1–205.7° C.;

(S)-3-(2,6-dimethylphenoxymethyl)piperidine hydrochloride, m.p. 228.4–229.8° C.;

3-(4-chloro-2,6-dimethylphenoxymethyl)piperidine hydrochloride, m.p. 176.1–178.2° C.

Example 2

Preparation of a Compound of Formula I
A. Preparation of I where $R^1$, $R^2$ and $R^6$ are Methyl, $R^3$ and $R^5$ are Hydrogen, and $R^4$ is Bromo 3-Hydroxymethyl-1-methylpiperidine (0.4 mL, 3.14 mmol) and triphenylphosphine (1.01 g, 3.85 mmol) were added to a solution of 4-bromo-2,6-dimethylphenol (517 mg, 2.57 mmol) in tetrahydrofuran (10 mL) at 0° C. under dry nitrogen, followed by the dropwise addition of diethyl azodicarboxylate (0.57 mL, 3.60 mmol). The mixture was stirred at 0° C. for 4 hours and the solvent removed in vacuo. The residue was purified on silica gel, eluting with 5% methanol in dichloromethane containing 0.25% ammonium hydroxide, to give 3-(4-bromo-2,6-dimethylphenoxymethyl)-1-methylpiperidine as an oil (531 mg, 66%).

The 3-(4-bromo-2,6-dimethylphenoxymethyl)-1-methylpiperidine was treated with 1N hydrochloric acid in ether, and the precipitated salt was recrystallized from acetonitrile/tert-butyl methyl ether to yield 3-(4-bromo-2,6-dimethylphenoxymethyl)-1-methylpiperidine hydrochloride, m.p. 180.9–183.5° C.

B. Similarly, following the procedures of Example 2A above, but replacing 4-bromo-2,6-dimethylphenol with other compounds of formula (1), other compounds of Formula I were prepared:

3-(2,6-dimethylphenoxymethyl)-1-methylpiperidine hydrochloride, m.p. 163.2–163.7° C.;

3-(4-fluoro-2,6-dimethylphenoxymethyl)-1-methylpiperidine fumarate, m.p. 155.4–155.9° C.;

3-(4-chloro-2,6-dimethylphenoxymethyl)-1-methylpiperidine hydrochloride, m.p. 160.1–161.3° C.;

3-(4-methoxy-2,6-dimethylphenoxymethyl)-1-methylpiperidine fumarate, m.p. 171.0–172.3° C.;

3-[4-(2,2,2-trifluoroethoxy)-2,6-dimethylphenoxymethyl]-1-methylpiperidine hydrochloride, m.p. 124.7–125.8° C.;

3-(2,4,6-trimethylphenoxymethyl)-1-methylpiperidine hydrochloride, m.p. 169.0–171.2° C.;

3-(2,6-dimethyl-4-phenylphenoxymethyl)-1-methylpiperidine hydrochloride, m.p. 243.6–244.6° C.;

3-phenoxymethyl-1-methylpiperidine hydrochloride, m.p. 155.2-156.2–156.2° C.;

3-(4-chlorophenoxymethyl)-1-methylpiperidine hydrochloride, m.p. 211.4–211.6° C.;

3-(4-bromophenoxymethyl)-1-methylpiperidine hydrochloride, m.p. 236.0–237.3° C.;

3-(4-methoxyphenoxymethyl)-1-methylpiperidine hydrochloride, m.p. 148.3–148.9° C.;

3-(2-methylphenoxymethyl)-1-methylpiperidine hydrochloride, m.p. 191.6–192.3° C.;

3-(3-methylphenoxymethyl)-1-methylpiperidine hydrochloride, m.p. 140.8–141.9° C.;

3-(4-methylphenoxymethyl)-1-methylpiperidine hydrochloride, m.p. 173.8–174.5° C.;

3-(2,4-dimethylphenoxymethyl)-1-methylpiperidine hydrochloride, m.p. 180.3–183.5° C.;

3-(3,5-dimethylphenoxymethyl)-1-methylpiperidine hydrochloride, m.p. 182.0–182.5° C.;

3-(4-bromo-2-methylphenoxymethyl)-1-methylpiperidine hydrochloride, m.p. 192.9–193.3° C.;

3-(2,6-dichlorophenoxymethyl)-1-methylpiperidine hydrochloride, m.p. 170.5–172.2° C.;

3-(2,6-dichloro-4-fluorophenoxymethyl)-1-methylpiperidine hydrochloride, m.p. 151.0–151.7° C.;

3-(2,4,6-trichlorophenoxymethyl)-1-methylpiperidine hydrochloride, m.p. 159.9–160.4° C.;

3-[2,6-dimethyl-4-(3-nitrophenyl)phenoxymethyl]-1-methylpiperidine hydrochloride, m.p. 198.5–199.5° C.; and 3-[4-(tert-butyldimethylsilyloxy)-2,6-dimethylphenoxymethyl]-1-methylpiperidine, $^1$H NMR (300 MHz, CDCl$_3$): γ 0.16 (s, 6H), 0.96 (s, 9H), 1.10–1.19 (m, 1H), 1.63–1.96 (m, 5H), 2.10–2.18 (m, 1H), 2.19 (s, 6H), 2.30 (s, 3H), 2.79 (br d, J=11 Hz, 1H), 3.11 (br d, J=11 Hz, 1H), 3.56 (d, J=6 Hz, 2H), 6.45 (s, 2H).

C. Alternatively, a solution of (R)-3-tosyloxymethyl-1-methylpiperidine (100 mg, 0.35 mmol), 4-bromo-2,6-dimethylphenol (75 mg, 0.37 mmol), and cesium carbonate (240 mg, 0.74 mmol) in dimethylformamide (4 mL) was heated to 65° C. under a nitrogen atmosphere for 1.5 hours. The solution was cooled to room temperature and partitioned between ethyl acetate (50 mL) and water (30 mL). The organic layer was removed and the aqueous phase extracted once more with ethyl acetate (30 mL). The combined acetate layers were dried over magnesium sulfate and concentrated to afford the (R)-3-(4-bromo-2,6-dimethylphenoxymethyl)-1-methylpiperidine as a clear oil. This material was identical to that prepared in Example 2E when analyzed by chiral HPLC (Chiralpak AD, 97:3:0.1 hexane/2-propanol/diethylamine).

D. Alternatively, formic acid (16.7 mL, 333 mmol) and aqueous formaldehyde (37%, 9.1 mL) were added dropwise to (S)-3-(4-bromo-2,6-dimethylphenoxymethyl)piperidine (24.1 g, 80.8 mmol) that was being chilled in an ice bath. After the addition was complete, the reaction was placed in an oil bath at a temperature of 95° C. for 4 hours. The mixture was cooled to room temperature and partitioned between 15% aqueous sodium hydroxide (200 mL) and ether (600 mL). The aqueous phase was extracted twice more with additional ether (300 mL), and the ether layers combined, washed with brine (150 mL), dried and concentrated. The residue was chromatographed on silica gel, eluting with acetone/hexanes (1:1) and concentrated to give (S)-3-(4-bromo-2,6-dimethylphenoxymethyl)-1-methylpiperidine as a clear oil.

The (S)-3-(4-bromo-2,6-dimethylphenoxymethyl)-1-methylpiperidine was dissolved in ether (600 mL) and treated with a 1M solution of hydrochloric acid in ether (90 mL). The resulting white precipitate was filtered and dried in vacuo to give (S)-3-(4-bromo-2,6-dimethylphenoxymethyl)-1-methylpiperidine hydrochloride (25.5 g, 87%), m.p. 209.7–210.5° C.

E. Similarly, replacing (S)-3-(4-bromo-2,6-dimethylphenoxymethyl)-piperidine with (R)-3-(4-bromo-2,6-dimethylphenoxymethyl)piperidine, and following the procedures of Example 2D above, the compound (R)-3-(4-bromo-2,6-dimethylphenoxymethyl)-1-methylpiperidine was prepared, m.p. 211.6–212.6° C.

Example 3

Alternative Preparation of a Compound of Formula I

A. Preparation of I where $R^1$, $R^2$, and $R^6$ are Methyl, $R^3$, $R^4$, and $R^5$ are Hydrogen A solution of 1M lithium aluminum hydride in tetrahydrofuran (45 mL, 45 mmol) was added dropwise during 30 minutes to (S)-N-(tert-butoxycarbonyl)-3-(2,6-dimethylphenoxymethyl)piperidine (13.0 g, 40.6 mmol) in dry tetrahydrofuran (250 mL) under a dry nitrogen atmosphere. After the addition was complete, the reaction mixture was heated at reflux for 4 hours, stirred at room temperature for 20 hours, and quenched by the cautious addition of solid sodium sulfate decahydrate (70 g). The sodium sulfate was removed by filtration and washed with ethyl acetate (3×150 mL). The combined filtrates were concentrated, and the residue chromatographed on silica gel, eluting with dichloromethane/methanol (9.5:0.5) to give (S)-3-(2,6-dimethylphenoxymethyl)-1-methylpiperidine as a clear oil (8.0 g).

The (S)-3-(2,6-dimethylphenoxymethyl)-1-methylpiperidine (8.0 g) was dissolved in ether (500 mL) and treated with a 1M solution of hydrochloric acid in ether (37.7 mL). The thick white precipitate was isolated by filtration, washed with ether (75 mL), and dried to give (S)-3-(2,6-dimethylphenoxymethyl)-1-methylpiperidine hydrochloride (8.6 g, 93%), m.p. 149.8–151.3° C.

B. Similarly, replacing (S)-N-(tert-butoxycarbonyl)-3-(2,6-dimethylphenoxymethyl)-piperidine with other compounds of formula (3), and following the procedures of Example 3A above, the following compounds of Formula I were prepared:

(R)-3-(2,6-dimethylphenoxymethyl)-1-methylpiperidine hydrochloride, m.p. 151.7–152.8° C.;

(S)-3-(4-chloro-2,6-dimethylphenoxymethyl)-1-methylpiperidine hydrochloride, m.p. 172.0–173.0° C.;

(S)-3-phenoxymethyl-1-methylpiperidine hydrochloride, m.p. 152.7–153.2° C.; and (R)-3-phenoxymethyl-1-methylpiperidine hydrochloride, m.p. 152.5–153.4° C.

Example 4

Alternative Preparation of a Compound of Formula I

A. Preparation of I where $R^1$ is Cyclopropylmethyl, $R^2$ and $R^6$ are Methyl, and $R^3$, $R^4$ and $R^5$ are Hydrogen Cyclopropylcarbonyl chloride (1.7 mL, 18 mmol) was added dropwise during 15 minutes to an ice cold mixture containing (S)-3-(2,6-dimethylphenoxymethyl)piperidine hydrochloride (4.4 g, 17 mmol), aqueous sodium bicarbonate (75 mL), and ethyl acetate (100 mL). After the addition was complete, the reaction was stirred at room temperature for 1 hour, and the resulting ethyl acetate layer was separated and concentrated. The residue was dissolved in dry tetrahydrofuran (125 mL) under a dry nitrogen atmosphere and a 1M solution of lithium aluminum hydride in tetrahydrofuran (18.9 mL) was added dropwise. When the addition was complete, the reaction mixture was heated to reflux for 2 hours, then cooled to room temperature. Solid sodium sulfate decahydrate (10 g) was slowly added with stirring and the mixture was filtered. The filtrate was concentrated and chromatographed on silica gel, eluting with acetone/hexanes (1:3) to give (S)-1-cyclopropylmethyl-3-(2,6-dimethylphenoxymethyl)piperidine as an oil.

The (S)-1-cyclopropylmethyl-3-(2,6-dimethylphenoxymethyl)piperidine was dissolved in dry ether (125 mL) and treated with 1M hydrochloric acid in ether (18.9 mL). The white precipitate was collected and dried under vacuum to give (S)-1-cyclopropylmethyl-3-(2,6-dimethylphenoxymethyl)-piperidine hydrochloride, (3.6 g, 66%), m.p. 137.3–137.5° C.

B. Similarly, replacing (S)-3-(2,6-dimethylphenoxymethyl)piperidine hydrochloride with other compounds of Formula Ia, and optionally replacing cyclopropylcarbonyl chloride with other acid chlorides, and following the procedures of Example 4A above, the following compounds of Formula I were prepared:

1-cyclopropylmethyl-3-(2,6-dimethylphenoxymethyl)piperidine hydrochloride, m.p. 147.5–148.0° C.;

(R)-1-cyclopropylmethyl-3-(2,6-dimethylphenoxymethyl)piperidine hydrochloride, m.p. 137.2–138.1° C.;

3-(2,6-dimethylphenoxymethyl)-1-ethylpiperidine hydrochloride, m.p. 157.2–160.0° C.;

3-phenoxymethyl-1-ethylpiperidine hydrochloride, m.p. 168.3–169.8° C.; and 3-phenoxymethyl-1-cyclopropylmethylpiperidine hydrochloride, m.p. 151.7–153.3° C.

Example 5

Alternative Preparation of a Compound of Formula I

Preparation of I where $R^1$ is 2-Dimethylaminoethyl, $R^2$ and $R^6$ are Methyl, and $R^3$, $R^4$ and $R^5$ are Hydrogen Chloroacetyl chloride (1.5 mL, 19 mmol) was added dropwise to a mixture of 3-(2,6-dimethylphenoxymethyl)piperidine hydrochloride (4.0 g, 16 mmol) in saturated aqueous sodium bicarbonate (70 mL) and ether (100 mL) that was cooled with an ice bath. After the addition was complete, the reaction mixture was stirred at room temperature for 2 hours. The ether layer was removed and concentrated, and the residue taken up in dry methanol (100 mL) while being cooled in an ice bath. Dimethylamine gas was bubbled into the solution slowly for 15 minutes, and the mixture was stirred at room temperature for 20 hours. The solvent was evaporated and the residue taken up in dry tetrahydrofuran (150 mL) under a nitrogen atmosphere, and a 1M solution of lithium aluminum hydride in tetrahydrofuran (17.2 mL) was added. The reaction mixture was heated under reflux for 4 hours and stirred at room temperature for 20 hours. Solid sodium sulfate decahydrate (25 g) was slowly added and the mixture filtered. The solid was washed twice with ethyl acetate (100 mL) and the combined organic layers were concentrated. The residue was partitioned between 10% aqueous hydrochloric acid (40 mL) and ether (50 mL). The aqueous layer was made alkaline with 50% potassium hydroxide and extracted with ether (3×50 mL). The combined ether layers were washed with brine (100 mL) and dried to give a solution of 3-(2,6-dimethylphenoxymethyl)-1-(2-dimethylaminoethyl) piperidine.

The 3-(2,6-dimethylphenoxymethyl)-1-(2-dimethylaminoethyl)piperidine solution was treated with a 1M solution of hydrochloric acid in ether (17.2 mL). The resulting precipitate was isolated by filtration, then dried under vacuum to give 3-(2,6-dimethylphenoxymethyl)-1-(2-dimethylaminoethyl)-piperidine hydrochloride (4.0 g, 71%), m.p. 263.2–263.5° C.

Example 6

Alternative Preparation of a Compound of Formula I

Preparation of I where $R^1$ is 3-Methanesulfonamidopropyl, $R^2$ and $R^6$ are Methyl, and $R^3$, $R^4$, and $R^5$ are Hydrogen 3-(2,6-Dimethylphenoxymethyl)piperidine hydrochloride (1.0 g, 3.9 mmol) was suspended in ethyl acetate (60 mL) and washed with 10% aqueous sodium hydroxide (50 mL). After the ethyl acetate layer was removed, dried, and concentrated, the residue was dissolved in dimethylformamide (15 mL). Potassium carbonate (0.65 g, 4.7 mmol) was added and then N-(3-chloropropyl)-methanesulfonamide (810 mg, 4.7 mmol) was added dropwise to the mixture which was then stirred at room temperature for 20 hours, at which time it was partitioned between ethyl acetate (100 mL) and water (100 mL). The aqueous phase was extracted with additional ethyl acetate (2×50 mL), and the combined ethyl acetate layers were washed with brine (60 mL), dried, and concentrated. The residue was chromatographed on silica gel, eluting with acetone/hexanes (1:1) containing 1% triethylamine, and concentrated to give 3-(2,6-dimethylphenoxymethyl)-1-(3-methanesulfonamido) propylpiperidine as a clear oil.

The 3-(2,6-dimethylphenoxymethyl)-1-(3-methanesulfonamido)propyl-piperidine was dissolved in ether (30 mL) and treated with 1M hydrochloric acid in ether (4.7 mL). The resulting white precipitate was isolated by filtration to give 3-(2,6-dimethylphenoxymethyl)-1-(3-methanesulfonamido)-propylpiperidine hydrochloride (650 mg, 43%), m.p. shrinks 51° C.

Example 7

Alternative Preparation of a Compound of Formula I

Preparation of I where $R^1$, $R^2$ and $R^6$ are Methyl, $R^3$ and $R^5$ are Hydrogen, and $R^4$ is Hydroxy To a solution of 3-[4-(tert-butyidimethylsilyloxy)-2,6dimethylphenoxymethyl]-1-methylpiperidine (3.2 g, 8.8 mmol) in tetrahydrofuran (50 mL) containing 20% acetic acid (5.5 mL, 19 mmol) at 0° C. was added 1M tetrabutylammonium fluoride in tetrahydrofuran (17.5 mL). The mixture was stirred from 0° C. to room temperature overnight and concentrated in vacua. The residue was partitioned between water and dichloromethane. The organic layer was dried and concentrated and the residue purified on silica gel, eluting with 5% methanol in dichloromethane containing 0.25% ammonium hydroxide, to give 3-(4-hydroxy-2,6-dimethylphenoxymethyl)-1 -methylpiperidine.

This product was converted to the hydrochloride salt and recrystallized from ethanol/tert-butyl methyl ether to give 3-(4-hydroxy-2,6-dimethylphenoxymethyl)-1-methylpiperidine hydrochloride (1.46 g, 58%), m.p. 224.5–225.5° C.

EXAMPLE 8

Preparation of Compounds of Formula I from Other Compounds of Formula I

Preparation of I where $R^1$, $R^2$ and $R^6$ are Methyl, $R^3$ and $R^5$ are Hydrogen, and $R^4$ is 3-Methoxyphenyl To a solution of 3-(4-bromo-2,6-dimethylphenoxymethyl)-1-methylpiperidine (531 mg, 1.70 mmol) in toluene (10 mL) was added 3-methoxyphenylboronic acid (319 mg, 2.10 mmol), tetrakis(triphenylphosphine)palladium(0) (58 mg, 0.05 mmol), and 2M sodium carbonate (1.7 mL, 3.4 mmol). The mixture was stirred at 100° C. overnight and cooled to room temperature. The solution was partitioned between water and ethyl acetate. The organic layer was washed twice with water, brine, and dried. The solvent was removed and the residue purified on silica gel, eluting with 5% methanol in dichloromethane containing 0.25% ammonium hydroxide, to give 3-[4-(3-methoxyphenyl)-2,6-dimethylphenoxymethyl]-1-methylpiperidine.

The product was converted to the hydrochloride salt and crystallized from ethyl acetate to give 3-[4-(3-methoxyphenyl)-2,6-dimethylphenoxymethyl]-1-methylpiperidine hydrochloride (301 mg, 45%), m.p. 175.2–178.8° C.

Example 9

Alternative Preparation of Compounds of Formula I from Other Compounds of Formula I Preparation of I where $R^1$, $R^2$, and $R^6$ are Methyl, $R^3$ and $R^5$ are Hydrogen, and $R^4$ is 3-Aminophenyl A mixture of 3-[2,6-dimethyl-4-(3-nitrophenyl) phenoxymethyl]-1-methylpiperidine (785 mg, 2.21 mmol), ethanol (10 mL), and ethyl acetate (5 mL) was hydrogenated overnight with platinum oxide (50 mg) at 1 atmosphere of hydrogen. The reaction was purged with nitrogen and filtered through Celite. The solids were washed with methanol and ethyl acetate. The filtrate and the washings were concentrated to give 3-[4-(3-aminophenyl)-2,6-dimethylphenoxymethyl]-1-methylpiperidine as a yellow oil (735 mg, quantitative).

A portion of the oil (175 mg) was treated with 1N hydrochloric acid in ether and crystallized from methanol/ether, to give 3-[4-(3-aminophenyl)-2,6-dimethylphenoxymethyl]-1-methylpiperidine dihydrochloride (193 mg), m.p. 272.3–273.9° C.

Example 10

Alternative Preparation of Compounds of Formula I from Other Compounds of Formula I Preparation of I where $R^1$, $R^2$, and $R^6$ are Methyl, $R^3$ and $R^5$ are Hydrogen, and $R^4$ is 3-Acetylaminophenyl To a solution of 3-[4-(3-aminophenyl)-2,6-dimethylphenoxymethyl]-1-methylpiperidine (513 mg, 1.58 mmol) in dichloromethane at 0° C. was added pyridine (1.3 mL, 16 mmol) and acetic anhydride (0.75 mL, 8.0 mmol). The mixture was stirred overnight at a temperature range from 0° C. to room temperature, and diluted with water and ethyl acetate. The aqueous layer was extracted with dichloromethane (3×), and the organic layers were dried and concentrated. The residue was purified on silica gel, eluting with 10% methanol/dichloromethane containing 0.5% ammonium hydroxide, to give 3-[4-(3-acetylaminophenyl)-2,6-dimethylphenoxymethyl]-1-methylpiperidine (479 mg, 82%).

The 3-[4-(3-acetylaminophenyl)-2,6-dimethylphenoxymethyl]-1-methylpiperidine was treated with 1N hydrochloric acid in ether and crystallized from methanol/tert-butyl methyl ether, to give 3-[4-(3-acetylaminophenyl)-2,6-dimethylph enxymethyl]-1-methylpiperidine hydrochloride, m.p. 231.0–231.9° C.

Example 11

Preparation of an N-Oxide of a Compound of Formula I

A. Preparation of an N-Oxide of I where $R^1$, $R^2$ and $R^6$ are Methyl, $R^3$ and $R^5$ are Hydrogen, and $R^4$ is Bromo (S)-3-(4-Bromo-2,6-dimethylphenoxymethyl)-1-methylpiperidine hydrochloride (338 mg, 0.97 mmol) was partitioned between ether and aqueous sodium hydroxide. The ether was dried and concentrated to give an oil which was dissolved in dichloromethane (10 mL). To this solution was added m-chloroperbenzoic acid (327 mg, 50–60%). After 30 minutes, the reaction mixture was diluted with dichloromethane, then washed once with 10% aqueous sodium thiosulfate and three times with aqueous sodium bicarbonate. After drying, the dichloromethane solution was concentrated and the residue recrystallized from ethyl acetate to give (S)-3-(4-bromo-2,6-dimethylphenoxymethyl)-1-methylpiperidine-N-oxide (90.1 mg), m.p. 210.0–211.0° C.

B. Similarly, replacing (S)-3-(4-Bromo-2,6-dimethylphenoxymethyl)-1-methylpiperidine hydrochloride with (S)-3-(2,6-dimethylphenoxymethyl)-1-methylpiperidine hydrochloride, and following the procedures of Example 11A above, (S)-3-(2,6-dimethylphenoxymethyl)-1-methylpiperidine-N-oxide was prepared, m.p. 203.5–204.8° C.

Example 12

This example illustrates the preparation of a representative pharmaceutical formulation for oral administration containing active compound of Formula I, e.g., (S)-3-(4-bromo-2,6-dimethylphenoxymethyl)-1-methylpiperidine hydrochloride.

| Ingredients | Quantity per tablet, mgs. |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula I can be used as the active compound in the preparation of the orally administrable formulations of this example.

Example 13

This example illustrates the preparation of another representative pharmaceutical formulation for oral administration containing an active compound of Formula I, e.g., (S)-3-(4-bromo-2,6-dimethylphenoxymethyl)-1-methylpiperidine hydrochloride.

| Ingredients | Quantity per tablet, mgs. |
|---|---|
| Active Compound | 400 |
| Cornstarch | 50 |
| Lactose | 145 |
| Magnesium stearate | 5 |

The above ingredients are mixed intimately and pressed into single scored tablets.

Other compounds of Formula I can be used as the active compound in the preparation of the orally administrable formulations of this example.

Example 14

This example illustrates the preparation of a representative pharmaceutical formulation containing an active compound of Formula I, e.g., (S)-3-(4-bromo-2,6-dimethylphenoxymethyl)-1-methylpiperidine hydrochloride.

An oral suspension is prepared having the following composition.

| Ingredients | |
|---|---|
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I can be used as the active compound in the preparation of the orally administrable formulations of this example.

Example 15

This example illustrates the preparation of a representative pharmaceutical formulation for oral administration containing an active compound of Formula I, e.g., (S)-3-(4-bromo-2,6-dimethylphenoxymethyl)-1-methylpiperidine hydrochloride.

An injectable preparation buffered to a pH of 4 is prepared having the following composition:

| Ingredients | |
|---|---|
| Active Compound | 0.2 g |
| Sodium Acetate Buffer Solution (0.4M) | 2.0 ml |
| HCl (1N) | q.s. to pH 4 |
| Water (distilled, sterile) | q.s. to 20 ml |

Other compounds of Formula I can be used as the active compound in the preparation of the injectable formulations of this example.

Example 16

This example illustrates the preparation of a representative pharmaceutical formulation for topical application containing an active compound of Formula I, e.g., 3-(4-bromo-2,6-dimethylphenoxymethyl)-1-methylpiperidine hydrochloride.

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I can be used as the active compound in the preparation of the topical formulations of this example.

Example 17

This example illustrates the preparation of a representative pharmaceutical formulation containing an active compound of Formula I, e.g., (S)-3-(4-bromo-2,6-dimethylphenoxymethyl)-1-methylpiperidine hydrochloride.

A suppository totalling 2.5 grams is prepared having the following composition:

| Ingredients | |
|---|---|
| Active Compound | 500 mg |
| Witepsol H-15* | balance |

*triglycerides of saturated vegetable fatty acid; a product of Riches-Nelson, Inc., New York, N.Y.

Other compounds of Formula I can be used as the active compound in the preparation of the suppository formulations of this example.

Example 18

Sodium Channel Blockade In Vitro Assay

This assay determines the effectiveness of compounds of Formula I as sodium channel blockers in an in vitro model by the inhibition of compound action potential propagation in isolated nerve preparations.

The sodium channel assay was performed as described in Kourtney and Stricharz *Local Anesthetics;* Springer-Verlag, New York, 1987. Briefly, the vagus nerves were removed from rats, continually superfusing them with control solutions or solutions of the compounds under test. Electric shocks were applied to the nerve to stimulate the propogation of nerve impulses. The amplitude of the synchronous compound action potential was measured; it was reduced as the sodium channels became blocked by the perfused compounds.

These studies suggest that the compounds of Formula I are potent use-dependent sodium channel blockers, particularly at higher frequencies, when tested by this method.

Example 19

Mechanical Allodynia In Vivo Assay

This assay determines the effectiveness of compounds of Formula I in relieving one of the symptoms in an in vivo model of neuropathic pain produced by spinal nerve ligation, namely mechanical allodynia.

Tactile allodynia was induced in rats using the procedures described by Kim and Chung, *Pain* 1992, 50:355–363. Briefly, the rats were anesthetized with an intraperitoneal dose of pentobarbital sodium (65 mg/kg) with additional doses of anesthetic given as needed. Each animal was then placed in a prone position, a 3 cm lateral incision was made, and the left paraspinal muscles separated from the spinous process at the $L_4$-$S_2$ level. The $L_6$ transverse process was then removed in order to visually identify the $L_4$-$L_6$ spinal nerves. The $L_5$ and $L_6$ spinal nerves were then individually isolated and tightly ligated with silk thread. The wound was then closed in layers by silk sutures. These procedures produced rats which developed a significant increase in sensitivity to mechanical stimuli that did not elicit a response in normal rats.

Mechanical sensitivity was assessed using a procedure described by Chaplan et al. *J. Neurosci. Methods* 1994, 53:55–63. Briefly, a series of eight Von Frey filaments of varying rigidity strength were applied to the plantar surface of the hind paw ipsilateral to the ligations with just enough force to bend the filament. The filaments were held in this position for no more than three seconds or until a positive allodynic response was displayed by the rat. A positive allodynic response consisted of lifting the affected paw followed immediately by licking or shaking of the paw. The order and frequency with which the individual filaments were applied were determined by using Dixon up-down method. Testing was initiated with the middle hair of the series with subsequent filaments being applied in consecutive fashion, either ascending or descending, depending on whether a negative or positive response, respectively, was obtained with the initial filament.

The results show that at one hour after oral administration, the compounds of Formula I had a minimum effective dose as low as 300 mg/kg. Overall, the compounds of the present invention were found to be effective in reversing mechanical allodynia-like symptoms when tested by this method.

Example 20

Cold Allodynia In Vivo Assay

This assay determines the effectiveness of compounds in relieving one of the symptoms of neuropathic pain produced by unilateral mononeuropathy, namely cold allodynia.

Unilateral mononeuropathy was produced in rats using the Chronic Constriction Injury model performed essentially as described by Bennet and Xie, *Pain* 1988, 33:87–107. Briefly, the rats were anesthetized with an intraperitoneal dose of pentobarbital sodium (65 mg/kg). The lateral aspect of each rat's hind limb was shaved and scrubbed with Novasan. Using aseptic technique, an incision was made on the lateral aspect of the hind limb at the mid-thigh level. The biceps femoris was bluntly dissected to expose the sciatic nerve. On the right hind limb of each rat, four loosely tied ligatures were made around the sciatic nerve approximately 1-2 millimeters apart. On the left side of each rat, an identical dissection was performed except that the sciatic nerve was not ligated. The muscle was closed with a continuous suture pattern, and the skin was closed with wound clips.

The rats demonstrating unilateral mononeuropathy were assessed for acute and chronic cold allodynia sensitivity. Briefly, each rat was placed individually into a plexiglass chamber with a metal plate 6 cm from the bottom. This chamber was filled with ice water to a depth of 2.5 cm above the metal plate, with the temperature of the bath maintained at 0° C. throughout the experiment. A timer was started, and the rat's response latency was measured to the nearest tenth of a second. A "response" was defined as a rapid withdrawal of the right ligated hindpaw completely out of the water while the animal was stationary and not pivoting. An exaggerated limp while the animal was walking was not scored as a response. Maximum immersion time was 20 seconds with a 20 minute interval between trials. The screening criteria were 1) the average of two trials was less than or equal to 13 seconds, and 2) there was consistency across the two trial scores. Animals were screened for hypersensitivity to cold on post-surgery days 4 through 10, and selected for inclusion in dose-response studies based on the criteria described above. The pre-dose screening values were used as the animal's baseline cold allodynia scores.

For acute studies, the animals received oral injections and were tested for cold allodynia at 1, 3, and sometimes 5 hours post-dose. The doses were based on the free base form of the compounds of Formula I. When tested in the acute cold allodynia assay, the compounds of Formula I generally demonstrated anti-allodynic effects at doses of 100 mg/kg. At higher doses (up to 600 mg/kg), inhibition of cold allodynia effects lasted up to 5 hours post-dose.

For chronic studies, the animals received oral injections of either vehicle (deionized water, 10 mL/kg) or compounds of Formula I (10 or 20 mg/kg), twice daily for 4 days and once on day 5. The animals were tested for allodynia on day 1 at 1, 3 and 5 hours following the 8 am dose, and at 5 hours following the 8 am dose on days 3 and 5. Two days later (day 7), the animals were tested for cold allodynia to assess whether there was a wash-out of the drug being tested. Following this screening for cold allodynia, the animals received oral injections of either vehicle or compounds of Formula I at a dose previously shown to produce significant anti-allodynic effects acutely (300 mg/kg po). One hour after this dosing, the animals were again tested for cold allodynia. For the chronic studies, the compounds of Formula I, administered orally at sub-threshold doses can produce as robust an anti-allodynic effect as a 15-fold higher acute doses (cf, 20 mg/kg chronic vs 300 mg/kg acute) on day 5 of dosing. After a 48-hour wash-out period at day 7, the animals were retested and were found to have returned to their baseline scores of allodynia, suggesting that the relief provided by the compounds of Formula I was symptomatic with no disease modifying effect on the underlying pathophysiology of the neuropathy. Importantly, the acutely active doses of the compounds of Formula 1 (300 mg/kg) administered at the end of the chronic studies (i.e., day 7) produced significant anti-allodynic effects, indicating that tolerance to the effects of chronic administration did not occur.

The long lasting, efficacious effects seen in this assay provide strong support for the utility of the compounds of the present invention in the treatment of neuropathic pain.

Example 21

Mechanical Hyperalgesia in Vivo Assay

This assay determines the effectiveness of compounds in relieving one of the symptoms of neuropathic pain produced by unilateral mononeuropathy, namely mechanical hyperalgesia.

A chronic constriction injury was produced by loosely ligating the right common sciatic nerve as described by Bennet and Xie, *Pain* 1988, 33:87–107. The left common sciatic nerve was visualized, but not manipulated to produce sham conditions.

The rats having a chronic constriction injury were assessed for mechanical hyperalgesia to a pin-prick stimulus as described by Koch et al. *Analgesia* 1996, 2(3), 157–164. Briefly, the rats were placed in individual compartments of a plexiglass box with a warmed, perforated metal floor. Hindpaw withdrawal duration was measured after a mild pin prick to the plantar surface of the ligated (right) and sham (left) hindpaws.

The compounds of the present invention produced a long lasting (5 hours) reversal of mechanical hyperalgesia elicited by a pin-prick stimulus in rats with a chronic constriction injury when tested by this method.

Example 22

Thermal Hyperalgesia In Vivo Assay

This assay determines the effectiveness of compounds in relieving one of the symptoms of neuropathic pain produced by unilateral mononeuropathy, namely thermal hyperalgesia.

The rats having had surgery as described in Example 21A were assessed for thermal hyperalgesia sensitivity at least 10 days post-surgery. Briefly, the rats were placed beneath inverted plexiglass cages upon an elevated glass platform and a radiant heat source beneath the glass was aimed at the plantar hindpaw. The duration of time before the hindpaw was withdrawn from the floor was measured to the nearest tenth of a second. The cutoff time for the heat stimulus was 20 seconds, and the light was calibrated such that this stimulus duration did not burn or blister the skin. Four latency measurements were taken for each hindpaw in each test session, alternating left and right hindpaws, with 5 minute intervals between tests. The latencies of each side were averaged and a difference score was obtained. From 12 days post-surgery, the pre-selected rats were randomly assigned to receive the drug or vehicle injections.

Oral administration of the compounds of the present invention produced potent and efficacious anti-hyperalgesic effects in rats with unilateral mononeuropathy. Doses up to 300 mg/kg were tested without adverse events. The potency and efficacy of the compounds of Formula I for inhibition of thermal hyperalgesia in rats with a unilateral mononeuropathy, taken together with its clean safety profile after oral administration, suggests that the compounds of the present invention will be therapeutically effective in treating neuropathic pain with a low probability of adverse events when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of Formula I:

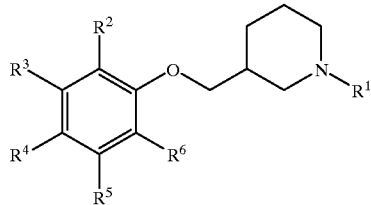

I where:
R$^1$ is (C1–4)alkyl, —(CH$_2$)$_m$cycloalkyl, or —(CH$_2$)$_m$NR$^7$SO$_2$R$^9$;
where:
  m is 1 to 3;
  R$^2$ and R$^6$ are each independently (C1–4)alkyl or halogen;
  R$^3$ and R$^5$ are each independently hydrogen or (C1–4)alkyl;
  R$^4$ is hydrogen, (C1–4)alkyl, hydroxy, (C1–4)alkyloxy, fluoro(C1–4)alkyloxy, halogen, or phenyl or mono- or di-substituted phenyl, the substituents selected from (C1–4)alkyloxy, amino, nitro, or acetylamino;
  R$^7$ and R$^8$ are each independently hydrogen or (C1–4)alkyl; and
  R$^9$ is (C1–4)alkyl;
or a pharmaceutically acceptable salt or N-oxide thereof, as an individual isomer or as a racemic or non-racemic mixture of isomers.

2. The compound of claim 1 where R$^1$ is (C1–4)alkyl, or —(CH$_2$)$_m$cycloalkyl.

3. The compound of claim 2 where R$^1$ is methyl, ethyl, or cyclopropylmethyl.

4. The compound of claim 3 where R$^2$ and R$^6$ are each independently methyl, ethyl, bromo, or chloro.

5. The compound of claim 4 where R$^3$ and R$^5$ are each independently hydrogen, methyl or ethyl.

6. The compound of claim 5 where R$^4$ is hydrogen or halogen.

7. The compound of claim 6 where R$^4$ is hydrogen, bromo, or chloro.

8. The compound of claim 1 where R$^1$, R$^2$ and R$^6$ are each independently methyl, R$^3$ and R$^5$ are each independently hydrogen, and R$^4$ is bromo.

9. The compound of claim 1 where R$^1$, R$^2$ and R$^6$ are each independently methyl, and R$^3$, R$^4$, and R$^5$ are each independently hydrogen.

10. The compound of claim 1 where the individual isomer is the (S)-isomer.

11. The compound of claim 1 where the pharmaceutically acceptable salt is hydrochloride.

12. A compound selected from the group consisting of:
 (a) 3-(4-bromo-2,6-dimethylphenoxymethyl)-1-methylpiperidine;
 (b) 3-(4-bromo-2,6-dimethylphenoxymethyl)-1-methylpiperidine N-oxide;
 (c) (S)-3-(4-bromo-2,6-dimethylphenoxymethyl)-1-methylpiperidine;
 (d) 3-(2,6-dimethylphenoxymethyl)-1-methylpiperidine;
 (e) 3-(2,6-dimethylphenoxymethyl)-1-methylpiperidine N-oxide;
 (f) S-3-(2,6-dimethylphenoxymethyl)-1-methylpiperidine;
 (g) 3-(2,6-dimethylphenoxymethyl)-1-cyclopropylmethylpiperidine; and pharmaceutically acceptable salts thereof.

13. The pharmaceutical composition comprising a therapeutically effective amount of a compound of claim 1 or a pharmaceutically acceptable salt or N-oxide thereof, in admixture with at least one pharmaceutically acceptable non-toxic excipient.

14. The pharmaceutical composition comprising a therapeutically effective amount of a compound or a pharmaceutically acceptable salt or N-oxide thereof, as in one of claims 9, 10 or 13, in admixture with at least one pharmaceutically acceptable non-toxic excipient.

15. The compound of claim 1 where R$^1$ is cyclopropylmethyl, R$^2$ and R$^6$ are each independently methyl, and R$^3$, R$^4$, and R$^5$ are each independently hydrogen.

* * * * *